United States Patent [19]

Prugnaud

[11] 4,057,620
[45] Nov. 8, 1977

[54] THERAPEUTIC COMPOSITION WITH MARKED POLYDETOXIFYING PROPERTIES, ESPECIALLY WITH REGARD TO TOBACCO

[75] Inventor: Robert Louis Prugnaud, Paris, France

[73] Assignee: Laboratoire Theranol, Paris, France

[21] Appl. No.: 457,634

[22] Filed: Apr. 3, 1974

Related U.S. Application Data

[63] Continuation-in-part of Ser. No. 116,660, Feb. 18, 1971, abandoned.

[30] Foreign Application Priority Data

Feb. 24, 1970 France .................................. 70.06599

[51] Int. Cl.² ...................... A61K 9/36; A61K 35/12; A61K 35/78; A61K 31/51
[52] U.S. Cl. ........................................ 424/35; 424/94; 424/195; 424/255; 424/258; 424/259; 424/263; 424/266; 424/280
[58] Field of Search ............................ 424/195, 35, 94

[56] References Cited

U.S. PATENT DOCUMENTS 2,283,817  5/1942  Martin ............................. 424/259 X
2,846,352  8/1958  Bryant ............................. 424/280 X

FOREIGN PATENT DOCUMENTS 1,093,877  12/1967  United Kingdom .................. 424/94

OTHER PUBLICATIONS

*Chemical Abstracts*, vol. 53, 18300–18301, (1969) vol. 50 (1962) 7446 & 13026; vol. 59, 4979–4980 (1963); vol. 63 (1965) 1662–1663.

*Primary Examiner*—Frederick E. Waddell
*Attorney, Agent, or Firm*—Oblon, Fisher, Spivak, McClelland & Maier

[57] ABSTRACT

A therapeutic detoxifying composition comprising a sympathoparalytic, vitamins from the groups B and C, and an organic salt of quinine. The composition may also contain an endogenous detoxifying substance. A preferred composition comprises Muramidase, nicotinamide, thiamine, ascorbic acid, pyridoxine, and a quinine salt having an organic anion, optionally with a sympathoparalytic sedative such as the dry extract of Crataegus root, all in specified proportions. The composition may be formulated with pharmaceutically acceptable carriers, and is markedly effective in detoxification therapy for solanaceous and ganglioplegic toxins such as nicotine and related toxic compounds.

7 Claims, No Drawings

THERAPEUTIC COMPOSITION WITH MARKED POLYDETOXIFYING PROPERTIES, ESPECIALLY WITH REGARD TO TOBACCO

CROSS-REFERENCE TO RELATED APPLICATIONS

This application is a continuation-in-part of Ser. No. 116,660, filed Feb. 18, 1971, now abandoned.

BACKGROUND OF THE INVENTION

1. Field of the Invention

This invention relates to a therapeutic detoxifying composition. More particularly, this invention relates to a therapeutic detoxifying composition comprising an endogenous detoxifying substance, vitamins of the groups B and C, an organic salt of quinine, and optionally, a sympathoparalytic sedative.

2. Description of the Prior Art

Various compositions have been proposed for the treatment of drug intoxication resulting from the use of solanaceous and ganglioplegic toxins such as nicotine and related toxic compounds, the most frequent intoxication with which is represented by the tobacco habit. While effective to some degree, one drawback of most detoxifying compositions is their specificity, which limits their use to treating particular types of intoxication. Another disadvantage of prior art compositions is their failure to reduce the temporary disequilibrium due to the arrested intake of toxins such as tobacco. A further drawback of those prior art compositions having polydetoxifying properties is the need to include relatively large amounts of each ingredient in order to achieve therapeutic results therefrom.

Due to accumulating clinical data on the dangers of smoking, a large amount of interest has been generated in detoxifying therapy for solanaceous and ganglioplegic toxins such as nicotine and related toxic derivatives. It would be desirable to have available a therapeutic composition with polydetoxifying properties which permit its use in treating various types of intoxications without necessitating large dosages of each ingredient. It would also be desirable if such a composition could reduce the temporary disequilibrium caused by the arrested intake of toxins such as tobacco. The present invention fills such needs.

SUMMARY OF THE INVENTION

Accordingly, one object of the present invention is to provide a therapeutic composition endowed with marked polydetoxifying properties, especially with regard to solanaceous and ganglioplegic toxins such as nicotine and related compounds.

Another object of the present invention is to provide a therapeutic composition having polydetoxifying properties which permit its use in treating various types of intoxications.

A further object of the present invention is to provide a polydetoxifying therapeutic composition wherein the ingredients synergistically enhance one another, enabling effective use of small dosages thereof.

A more specific object of the present invention is to provide a polydetoxifying composition especially suitable for therapeutically treating intoxication resulting from the use of solanaceous and ganglioplegic toxins such as nicotine and related toxic compounds, which restores the state of equilibrium disrupted by the arrested use of tobacco.

Briefly, these and other objects are obtained in one aspect of the present invention which provides a therapeutic detoxifying composition comprising nicotinamide, thiamine, ascorbic acid, pyridoxine, and a quinine salt having an organic anion, optionally with Muramidase and/or a sympathoparalytic sedative such as the dry extract of Crataegus root, all in specified proportions. The composition may be formulated with pharmaceutically acceptable carriers, and is markedly effective in detoxification therapy for solanaceous and ganglioplegic toxins such as nicotine and related toxic compounds.

The above and other objects, features, and advantages of the invention will become more fully apparent to those skilled in the art from the following description and examples of preferred embodiments of the invention, which are presented by way of example and not by way of limitation.

DESCRIPTION OF THE PREFERRED EMBODIMENTS

The compositions of the present invention endowed with marked polydetoxifying properties, especially with regard to tobacco, comprise an endogenous detoxifying substance, vitamins of the groups B and C, an organic salt of quinine, and, optionally, a sympathoparalytic sedative. They may be formulated with conventional binders or pharmaceutically acceptable carriers.

The composition of this invention may contain an endogenous detoxifying substance, such as Muramidase (egg white lysozyne). Muramidase is a naturally occurring substance which plays a role in the defense mechanism of organisms. Additionally, Muramidase has an enzymatic activity which produces in man an attenuation of the nociceptive effects of toxic substances such as nicotine. As used in the most preferred form of its purified base, Muramidase also exhibits a synergistic action on all of the detoxifying properties of the composition of the present invention.

The second active ingredient, which is optional but preferably included in the composition of the present invention, is a sympathoparalytic sedative such as a totally dry extract of crataegus root. The main active ingredient of Crataegus extract is an alkaloid, vinetine or oxyacanthine. Vinetine is a white crystalline powder with a bitter taste, the melting point of which is about 216° C. It is practically insoluble in water, although it is soluble in alcohol, chloroform and ether. It has regulating powers over the parasympathetic system. By regulating the parasympathetic system, this ingredient has an essential effect, in the case of tobacco intoxication, of attenuating the habitual nervousness of the smoker.

Nicotinamide, or vitamin PP, functions to reestablish cellular metabolism by its action at the level of the oxidation-reduction coenzymes. It has a preventive action on vascular alterations, and a strong antitoxic power.

Thiamine, or vitamin B1, normalizes glucose metabolism as well as possessing a slight vasotonic and cardiotonic action. It is endowed with neurotropic properties which are especially accentuated in the form of the mononitrate, which is also more stable than the hydrochloride form.

Ascorbic acid, or vitamin C, potentializes the action of the totally dry extract of Crataegus root as well as that of the quninine salt. It reduces the stress on the cortico-suprarenal glands, which appears in intoxications caused by parasympholytic or ganglioplegic toxins, such as nicotine and its close toxic derivatives.

Pyridoxine, or vitamin B6, is a factor in cardio-vascular and neurologic protection. It has a detoxifying action in itself, which is further amplified by the presence of vitamin C.

The quinine salt used in the medicament of the invention is an organic derivative which can be either the malate, the pyruvate, the ascorbate or the lactate of quinine. The choice of the organic salts of quinine is determined by the fact that they are more active than the mineral salts in the activation of their detoxifying properties. The detoxifying action which is sought is based on the possibility of the substitution in the organism of the quinine instead of a ganglioplegic or a sympathoparalytic, which is true of nicotine and its close toxic derivatives. This substitution is all the more facilitated because the quinine is used in well determined and small doses.

It is important to note that the smoker, deprived of the need to smoke by the effect of the present composition, is in a state of a temporary disequilibrium due to the arrest of the use of tobacco. It is here that one of the essential qualities of this invention lies, as the entire group of its ingredients constitutes a detoxifying "synergic entity" designated to reestablish the equilibrium of the smoker and to combat the stress which results from the suppression of tobacco.

In summary, the invention has a double action: it permits the suppression of the use of tobacco in the intoxicated smoker and it reestablishes the equilibrium of the smoker during his stage of tobacco deprivation.

Pharmacological studies on guinea-pigs have demonstrated, among other results, that the limination of the quinine is very gradual; it begins in 15 minutes, is maximal in 6 hours, and ends in 48 hours.

The clinical experiments using the composition of the invention have produced evidence of particularly interesting results in highly tobacco-intoxicated persons who were resistant to all types of therapeutics previously attempted. In such persons, stoppage of the tobacco habit is often observed in the first 15 days following the beginning of the treatment; in other persons whose treatment required one month and sometimes more, it is then necessary to provide a second cure.

Among light smokers (one package of cigarettes per day), stoppage of the tobacco in general is achieved in the first week of treatment.

The number of failures observed have been small, of the order of only 15% on the entire group of patients. After verification of these failures, they were found to be most often imputable either to irregularity in following the treatment doses, or to the fact that the treatments were stopped prematurely.

The usual treatment with this composition requires one month, and the product should be taken regularly four times per day.

Another feature of the invention is that the active principles are associated in a pharmaceutically acceptable vehicle. The therapeutic properties of each of the ingredients are already partially known and utilized separately in human therapeutics.

Below, non-limiting examples are given of formulas for the composition of this invention. While Muramidase, pyridoxine, nicotinamide, and the quinine organic salt may be present in an amount ranging from 1.5 to about 150 mg., preferred dosages are from about 10 to 20 mg. Similarly, ascorbic acid may be present in amounts ranging from about 7.5 to 750 mg., with a preferred range being from about 50 to 100 mg. Thiamine may be present in an amount ranging from 2.25 to 225 mg., with a preferred amount being from about 15 to 30 mg. Crataegus root extract, when utilized, may be present in an amount ranging from 4.5 to 450 mg., preferably from about 30 to 60 mg.

| Formula No. 1 - Sugar-coated tablets: | |
|---|---|
| Muramidase purified base | 10 mg |
| Crataegus extract | 30 mg |
| Pyridoxine Hydrochloride | 10 mg |
| Ascorbic acid | 50 mg |
| Thiamine mononitrate | 15 mg |
| Nicotinamide | 10 mg |
| Quinine ascorbate | 10 mg |
| Excipient qsp one tablet for 300 mg | |
| The dosage is 8 tablets per day, at the rate of 2 tablets each 4 hours. | |

| Formula No. 2 - Sugar-coated tablets "strong formula" | |
|---|---|
| Muramidase purified base | 20 mg |
| Crataegus extract | 60 mg |
| Pyridoxine hydrochloride | 20 mg |
| Ascorbic acid | 100 mg |
| Thiamine mononitrate | 30 mg |
| Nicotinamide | 20 mg |
| Quinine ascorbate | 20 mg |
| Excipient qsp one tablet for 400 mg | |
| The dosage is 4 tablets per day, at the rate of 1 tablet each 4 hours | |

The following formulations, do not contain Muramidase.

| Formula No. 3 - Potable solution administrable by dilution of a suitable number of drops | |
|---|---|
| Vinetine | 500 mg |
| Vitamin B6 | 500 mg |
| Ascorbic Acid | 250 mg |
| Vitamin B1 | 750 mg |
| Vitamin PP | 500 mg |
| Quinine Malate | 250 mg |
| Sufficient flavored distilled water for 10 ml | |

| Formula No. 4 - Formula for coated tablets | |
|---|---|
| Vinetine | 10 mg |
| Vitamin B6 | 10 mg |
| Ascorbic Acid | 5 mg |
| Vitamin B1 | 15 mg |
| Vitamin PP | 10 mg |
| Quinine Ascorbate | 8 mg |
| Inert ingredients to make one tablet of 200 mg | |

It will be appreciated that while the foregoing disclosure relates to preferred embodiments of the invention effective in detoxification therapy for solanaceous and ganglioplegic toxins, such as nicotine and related compounds, it is capable of numerous modifications or alterations which may be made by those skilled in the art without departing from the spirit and scope of the invention as set forth in the appended claims.

What is claimed as new and intended to be covered by Letters Patent is:

1. A therapeutic detoxifying composition comprising:
   a. extract of Crataegus
   b. a vitamin selected from the group consisting of vitamins PP, B, $B_1$, $B_6$ and C, and c. an organic salt of quinine selected from the group consisting of ascorbate, lactate, malate and pyruvate wherein (a), (b) and (c) are present in weight ratios of 4.5 to 450(a) to 7.5 to 750(b) and 1.5 to 150(c).

2. The composition of claim 1 which further contains
d. Muramidase in a weight ratio of 1.5 to 150.

3. The composition of claim 2 in a pharamaceutically acceptable carrier.

4. The composition of claim 2 in which the extract of Crataegus contains as its main active ingredient vinetine, and is present in about 3 parts.

5. A therapeutic detoxifying composition comprising, in parts by weight:

a. One part Muramidase;
b. About one part pyridoxine;
c. About five parts ascorbic acid;
d. About one and one-half parts thiamine;
e. About one part nicotinamide;
f. About one part of an organic salt of quinine selected from the group consisting of ascorbate, lactate, malate, and pyruvate;
g. About 3 parts dry extract of Crataegus root.

6. The composition of claim 2, wherein said Muramidase is present in an amount ranging from about 10 to about 20 mg.

7. The composition of claim 2 in form of sugar coated tablets.

* * * * *